United States Patent [19]

Steiner

[11] 3,953,524

[45] Apr. 27, 1976

[54] CATALYTIC HYDROGENATION OF ALPHA,BETA-UNSATURATED ALDEHYDES TO ALPHA,BETA-UNSATURATED ALCOHOLS

[75] Inventor: Kurt Steiner, Starrkirch, Switzerland

[73] Assignee: Hoffmann-La Roche Inc., Nutley, N.J.

[22] Filed: Mar. 11, 1974

[21] Appl. No.: 450,134

[30] Foreign Application Priority Data
Mar. 21, 1973 Switzerland............................ 4098/73

[52] U.S. Cl. .................. 260/617 A; 260/611 R; 260/611 B; 260/618 R; 260/638 B; 260/614 R; 260/484 R; 260/631.5; 260/618 F; 260/347.8; 260/297 R; 260/293.9
[51] Int. Cl.² ........................................ C07C 29/14
[58] Field of Search......... 260/638 B, 617 A, 618 F, 260/611 R, 611 B, 614 R, 631.5

[56] References Cited
UNITED STATES PATENTS

| | | | |
|---|---|---|---|
| 2,448,047 | 8/1948 | Peppel............................ | 260/638 B |
| 2,760,994 | 8/1956 | Gwynn............................. | 252/472 |
| 3,284,517 | 11/1966 | Rylander et al................. | 260/638 B |
| 3,591,656 | 7/1971 | Kroll............................... | 260/618 H |

FOREIGN PATENTS OR APPLICATIONS

| | | | |
|---|---|---|---|
| 1,123,837 | 8/1968 | United Kingdom............. | 260/638 B |

OTHER PUBLICATIONS

Hotta et al., Bulletin of the Chemical Society of Japan, Vol. 44, pp. 1348–1352 (1971).

*Primary Examiner*—James O. Thomas, Jr.
*Assistant Examiner*—James H. Reamer
*Attorney, Agent, or Firm*—Samuel L. Welt; Bernard S. Leon; William H. Epstein

[57] ABSTRACT

Improved, selective hydrogenation of alpha, beta-unsaturated aldehydes to alpha,beta-unsaturated alcohols utilizing a platinum-cobalt catalyst.

15 Claims, No Drawings

CATALYTIC HYDROGENATION OF ALPHA,BETA-UNSATURATED ALDEHYDES TO ALPHA,BETA-UNSATURATED ALCOHOLS

BACKGROUND OF THE INVENTION

It is well known that aldehydes can be reduced to corresponding alcohols. However, while the catalytic reduction of saturated aldehydes generally proceeds without trouble, difficulties are frequently encountered in selectively reducing unsaturated aldehydes to the corresponding alcohols.

With regard to alpha, beta-unsaturated aldehydes, the selective reduction of the formyl group is made even more difficult by the propensity of the carbon-carbon double bond, adjacent to the formyl group, to be simultaneously hydrogenated. Still greater difficulties are encountered when, besides the alpha, beta-unsaturated double bond, additional, reducible, double or triple-bonds, which may be conjugated, and/or other reducible groups are present in the aldehyde.

SUMMARY OF THE INVENTION

In accordance with the process of this application, an alpha, beta-unsaturated alcohol is obtained by hydrogenating an alpha, beta-unsaturated aldehyde in a solvent in the presence of a platinum-cobalt catalyst which contains 1 to 100 moles of platinum per mole of cobalt. By this process, yields of up to about 99+% of the alpha, beta-unsaturated alcohol can be obtained.

DETAILED DESCRIPTION OF THE INVENTION

By the process of this application, any alpha, beta-unsaturated aldehyde can be reduced to the corresponding alpha, beta-unsaturated alcohol. Among the alpha, beta-unsaturated aldehydes which can be reduced by the process of this application are the hydrocarbonyl, cyclohydrocarbyl, aryl, and heterocyclic, alpha, beta-unsaturated aldehydes. Included among the hydrocarbyl, cyclohydrocarbyl, aryl and heterocyclic, alpha, beta-unsaturated aldehydes which can be reduced by this process are the unsubstituted aldehydes and the aldehydes substituted with one or more hydroxy, lower alkoxy, lower alkanoyloxy, lower alkoxycarbonyl and/or ketalized oxo substituents as well as one or more hydrocarbyl, cyclohydrocarbyl and/or aryl substituents.

Among the preferred alpha, beta-unsaturated aldehydes in the process of this application are the compounds of the formula:

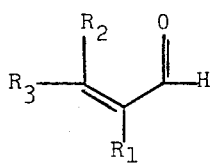

I wherein $R_1$ and $R_2$ are hydrogen or lower alkyl; and $R_3$ is hydrocarbyl, cyclohydrocarbyl or aryl; or $R_1$ and $R_3$, taken together, or $R_2$ and $R_3$, taken together, form a carbocyclic or heterocyclic group; which can be converted by hydrogenation in the presence of the cobalt-platinum catalyst to an alpha, beta-unsaturated alcohol of the formula:

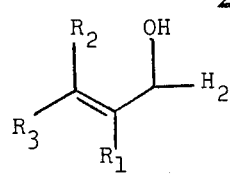

II wherein $R_1$, $R_2$ and $R_3$ are as above.

Among the compounds of formula I, particularly preferred alpha, beta-unsaturated aldehydes include compounds of the formula:

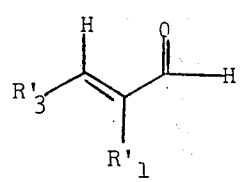

I-A wherein $R'_1$ and $R'_3$, taken together, form an olefinically unsaturated or aromatic, carbocyclic or heterocyclic group; such as veratraldehyde, vanillin, furfural, alpha- or beta-naphthyl aldehyde and beta-cyclocitral, which can be converted to an alpha, beta-unsaturated alcohol of the formula:

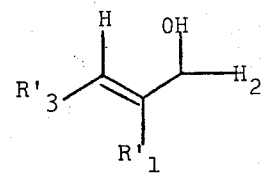

II-A wherein $R'_1$ and $R'_3$ are as above; such as veratryl alcohol, vanillic alcohol, furfuryl alcohol, alpha- or beta-naphthyl carbinol and beta-cyclogeraniol.

Also among the compounds of formula I, particularly preferred alpha, beta-unsaturated aldehydes include the compounds of the formula:

R''₂   O
 \    ||
  C = C-H       I-B
 /    |
R''₃  H wherein $R''_2$ and $R''_3$, taken together, form a cyclohydrocarbyl; such as cyclopentylidenacetaldehyde, cyclohexylidenacetaldehyde, 2,6,6-trimethyl-cyclohexylidenacetaldehyde and 3-methoxy-19-nor-pregnan-1,3,5,17(20)-tetraen-21-al, which can be converted to an alcohol of the formula:

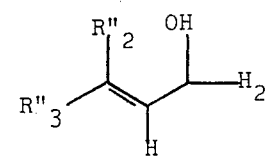

II-B wherein R″$_2$ and R″$_3$ are as above; such as cyclopentylidenethyl alcohol, cyclohexylidenethyl alcohol, 2,6,6-trimethyl-cyclohexylidenethyl alcohol, and 3-methoxy-19-nor-pregna-1,3,5,17(20)-tetraen-21-ol.

Further among the compounds of formula I, particularly preferred alpha, beta-unsaturated aldehydes include compounds of the formula:

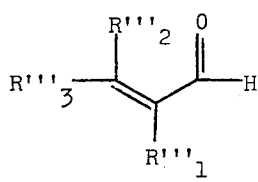

I-C wherein R‴$_1$ and R‴$_2$ are hydrogen or lower alkyl; and R‴$_3$ is cyclohydrocarbyl or aryl; such as cinnamaldehyde, alpha-pentylcinnamaldehyde, alpha-hexylcinnamaldehyde, and 3-[3-methyl-cyclohex-3-en-1-yl]-but-2-en-1-al, which can be converted to an alcohol of the formula:

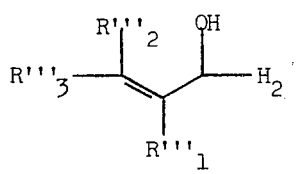

II-C wherein R‴$_1$, R‴$_2$ and R‴$_3$ are as above; such as cinnamic alcohol, alpha-pentylcinnamic alcohol, alpha-hexyl-cinnamic alcohol, and 3-[3-methyl-cyclohex-3-en-1-yl]-but-2-en-1-ol.

Still further among the compounds of formula I, particularly preferred alpha, beta-unsaturated aldehydes include compounds of the formula:

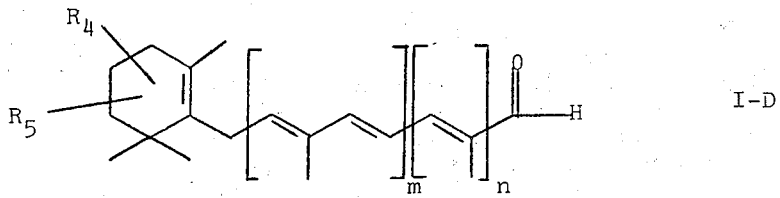

I-D wherein $m$ and $n$ are the integer 0 or 1; R$_4$ is hydrogen or hydroxy; R$_5$ is hydrogen; or R$_4$ and R$_5$, taken together, form a ketalized oxo; either $m$ or $n$ being 1; such as 4-[2,6,6-trimethyl-cyclohex-1-en-1-yl]-2-methyl-but-2-en-1-al, 6-[2,6,6-trimethyl-cyclohex-1-en-1-yl]-4-methyl-hexa-2,4-dien-1-al and 8-[2,6,6-trimethyl-cyclohex-1-en-1-yl]-2,6, dimethyl-octa-2,4,6-trien-1-al, which can be converted to an alcohol of the formula:

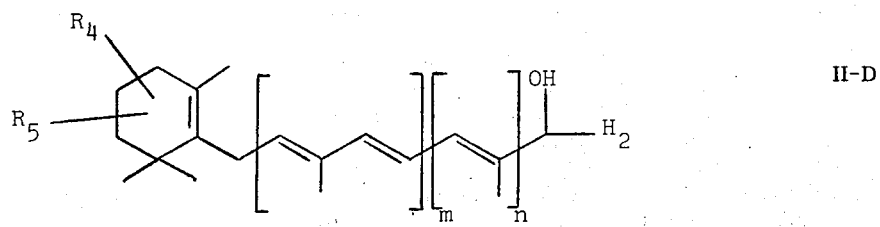

II-D wherein $m$, $n$, R$_4$ and R$_5$ are as above; such as 4-[2,6,6-trimethyl-cyclohex-1-en-1-yl]-2-methyl-but-2-en-1-ol, 6-[2,6,6-trimethyl-cyclohex-1-en-1-yl]-4-methyl-hexa-2,4-dien-1-ol and 8-[2,6,6-trimethyl-cyclohex-1-en-1-yl]-2,6,6-dimethyl-octa-2,4,6-trien-1-ol.

Also among the compounds of formula I, particularly preferred alpha, beta-unsaturated aldehydes include compounds of the formula:

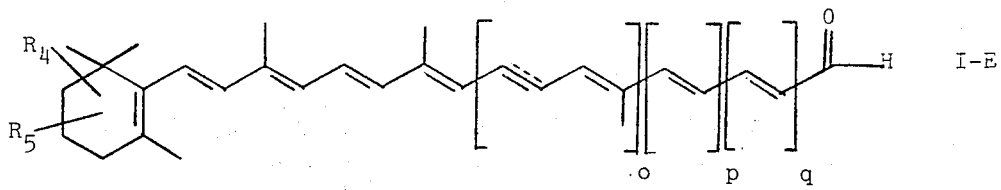

I-E wherein R$_4$ and R$_5$ are as above; the dotted bond can optionally be hydrogenated; and $o$, $p$, and $q$ are the integer 0 or 1; provided that when $o$ is 0, $p$ and $q$ are 0, when $p$ is 1, $o$ is 1, and when $p$ is 0, $q$ is 0; such as vitamin A aldehyde, 13-[2,6,6-trimethyl-cyclohex-1-en-1-yl]-2,7,11-trimethyl-trideca-2,6,8,10,12-pentaen-4-yn-1-al, 15-[2,6,6-trimethyl-cyclohex-1-en-1-yl]-

4,9,13-trimethyl-pentadeca-2,4,8,10,12,14-hexaen-6-yn-1-al and 17-[2,6,6-trimethyl-cyclohex-1-en-1-yl]-2,6,11,15-tetramethyl-heptadeca-2,4,6,10,12,14,16-heptaen-8-yn-1-al, which can be converted to an alcohol of the formula:

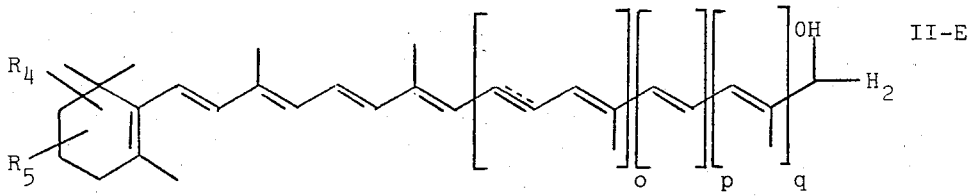

wherein $R_4$, $R_5$, $o$, $p$, $q$ and the dotted bond are as above; such as vitamin A alcohol, 13-[2,6,6-trimethyl-cyclohex-1-en-1-yl]-2,7,11-trimethyl-trideca-2,6,8,10,12-pentaen-4-yn-1-ol, 15-[2,6,6-trimethyl-cyclohex-1-en-1-yl]-4,9,13-trimethyl-pentadeca-2,4,8,10,12,14-hexaen-6-yn-1-ol and 17-[2,6,6-trimethyl-cyclohex-1-en-1-yl]-2,6,11,15-tetramethyl-heptadeca-2,4,6,10,12,14,16-heptaen-8-yn-1-ol.

Further among the compounds of formula I, particularly preferred alpha, beta-unsaturated aldehydes include compounds of the formula:

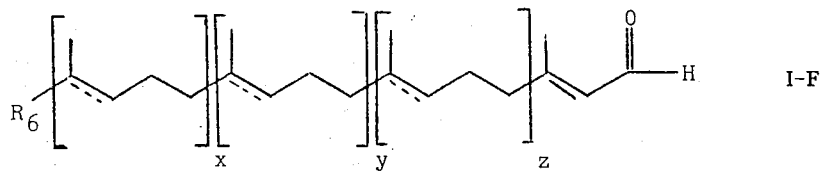

wherein $R_6$ is lower alkyl or lower alkenyl or lower alkoxy or lower alkanoyloxy substituted lower alkyl or lower alkenyl; $x$, $y$, and $z$ are the integer 0 or 1; with the proviso that when $z$ is 0, $x$ and $y$ are 0, when $y$ is 1, $z$ is 1 and when $y$ is 0, $x$ is 0; the $x$, $y$ and $z$ segments can be optionally lower alkyl, hydroxy or lower alkoxy substituted; and the dotted bonds can be optionally hydrogenated; such as prenal, 4,4-dimethoxy-3-methyl-but-2-en-1-al, 3-methyl-pent-2-en-1-al, 6-acetoxy-3-methyl-hexa-2,4-dien-1-al, 3,6,7-trimethyl-oct-2,6-dien-1-al, 3,7-dimethyl-7-methoxy-oct-2-en-1-al, 7-ethyl-3-methyl-nona-2,6-dien-1-al, citral, 7-hydroxy-dihydrocitral, 7-methoxy-dihydrocitral, farnesal, geranylcitral and phytal, which can be converted to an alcohol of the formula:

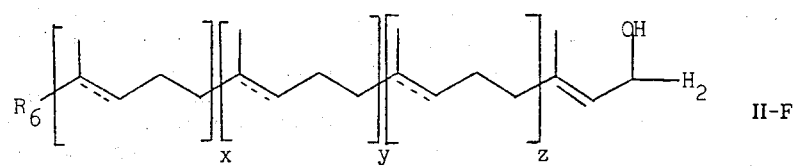

wherein $R_6$, $x$, $y$, $z$ and the dotted bonds are as above; such as prenol, 4,4-dimethoxy-3-methyl-but-2-en-1-ol, 3-methyl-pent-2-en-1-ol, 6-acetoxy-3-methyl-hexa-2,4-dien-1-ol, 3,6,7-trimethyl-octa-2,6-dien-1-ol, 3,7-dimethyl-4-ethyl-octa-2,6-dien-1-ol, 3,7-dimethyl-7-methoxy-oct-2-en-1-ol, 7-ethyl-3-methyl-nona-2,6-dien-1-ol, geraniol, 7-hydroxy-dihydrogeraniol, 7-methoxy-dihydrogeraniol, farnesol, geranylgeraniol, and phytol.

Still further among the compounds of formula I, particularly preferred alpha, beta-unsaturated aldehydes include compounds of the formula:

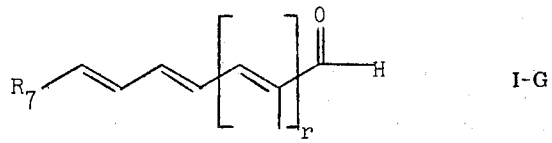

wherein $R_7$ is lower alkanoyloxy; and $r$ is the integer 0 or 1; such as 6-acetoxy-4-methyl-hexa-2,4-dien-1-al and 8-acetoxy-2,6-dimethyl-octa-2,4,6-trien-1-al, which can be converted to an alcohol of the formula:

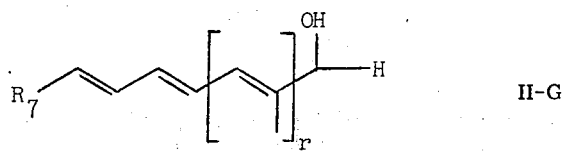

wherein $R_7$ and $r$ are as above; such as 6-acetoxy-4-methyl-hexa-2,4-dien-1-ol and 8-acetoxy-2,6-dimethyl-octa-2,4,6-trien-1-ol.

As used throughout this application, the term "hydrocarbyl" denotes a monovalent, straight chain or branched chain aliphatic substituent consisting solely of carbon and hydrogen. The hydrocarbyl group can be saturated or unsaturated in one or more positions.

Among the hydrocarbyl groups are included alkyl groups containing from 1 to 30 carbon atoms and alkenyl and alkynyl groups containing from 2 to 30 carbon atoms. The hydrocarbyl group can be unsubstituted or substituted in one or more positions with lower alkyl, cyclohydrocarbyl, aryl, lower alkoxy, hydroxy, ketalized oxo, lower alkanoyloxy, and lower alkoxycarbonyl groups.

As also used throughout this application, the term "cyclohydrocarbyl" denotes a mononuclear or polynuclear, monovalent, cycloaliphatic substituent consisting solely of carbon and hydrogen. The cyclohydrocarbyl group can be saturated or unsaturated in one or more positions. Among the cyclohydrocarbyl groups are the mononuclear, cycloalkyl and cycloalkenyl groups of 3 to 8 carbon atoms, such as cyclohexyl and cyclopentenyl. The cyclohydrocarbyl group can be unsubstituted or substituted in one or more positions with lower alkyl, lower alkoxy, hydroxy, ketalized oxo, lower alkanoyloxy and lower alkoxycarbonyl groups. The substituted and unsubstituted cyclohydrocarbyl group can include from 3 to 20 carbon atoms.

As further used throughout this application, the term carbocyclic group comprehends mononuclear and polynuclear, cyclic groups consisting solely of carbon and hydrogen. Among the carbocyclic groups are the saturated and olefinically unsaturated cyclohydrocarbyl groups of 3 to 20 carbon atoms, such as cyclopropyl, cyclohexyl and cyclopentenyl, and the aromatic hydrocarbon groups of 6 to 14 carbon atoms, such as phenyl and naphthyl. The carbocyclic group can be unsubstituted or substituted in one or more positions with lower alkyl, lower alkoxy, hydroxy, ketalized oxo, lower alkanoyloxy or loweralkoxy carbonyl groups.

As still further used throughout this application, the term "heterocyclic group" comprehends mononuclear and polynuclear, saturated, olefinically unsaturated and aromatic groups of 5 to 14 members containing one or more oxygen, nitrogen or sulphur atoms. Among the heterocyclic groups are the mononuclear groups, such as furyl, pyridyl and piperidyl, and the polynuclear groups, such as the groups formed by condensing a mononuclear, heterocyclic group with one or more, mononuclear cycloalkyl groups, as for example, carbazolyl. The preferred heterocyclic groups are the mononuclear groups of 5 or 6 members.

Also in this application, the term "lower alkyl" comprehends branched chain and straight chain, saturated aliphatic hydrocarbyl groups containing 1 to 6 carbon atoms, such as methyl ethyl, propyl and isopropyl. Also herein, the term "lower alkoxy" comprehends lower alkyloxy groups containing 1 to 6 carbon atoms such as methoxy and isopropoxy. As further used herein. the term "lower alkanoyloxy" comprehends lower alkyl acyloxy groups containing 1 to 6 carbon atoms such as formyloxy, acetyloxy, propionyloxy, and butyryloxy. As still further used herein, the term aryl comprehends monocyclic and polynuclear, aromatic hydrocarbon groups of 6 to 14 carbon atoms which are unsubstitute or substituted in one or more positions with a lower alkylenedioxy, lower alkyl, halogen, nitro or lower alkoxy group.

As still further used throughout this application, the term "aliphatic" with reference to a hydrocarbyl or cyclohydrocarbyl group denotes substituents containing no aromatic unsaturation but which can be otherwise saturated or unsaturated, i.e., an alkyl or a group containing olefinic and/or acetylenic unsaturation. Also herein, the term "ketalized oxo" comprehends derivatives of an oxo group formed by reaction thereof with a lower alkanediol, preferably ethylene glycol, or a lower alkanol, preferably methanol, to yield a lower alkylenedioxy group. The preferred lower alkylenedioxy groups are the groups having 1 to 4 carbon atoms, particularly methylenedioxy and ethylenedioxy. Further herein, the term "halogen" or "halo", unless otherwise stated, comprehends fluorine, chlorine, bromine and iodine.

In accordance with the process of this application, an alpha, betaunsaturated aldehyde is hydrogenated in a solvent in the presence of a platinum-cobalt catalyst which contains platinum and cobalt in a ratio of about 1 to 100 atoms of platinum per atom of cobalt. The platinum-cobalt catalyst of this application comprises elemental platinum having a surface coated with elemental cobalt. The preferred form of the platinum-cobalt catalyst of this application is a suspension of the catalyst in an inert solvent, preferably a suspension in a solvent suitable for dissolving the aldehyde or in a solvent which is entirely miscible with a solvent suitable for dissolving the aldehyde.

The platinum-cobalt catalyst of this application can be prepared as a suspension in a solvent in a conventional manner.

Preferably, the catalyst is obtained as a suspension by first suspending the required amount of platinum oxide in an inert liquid medium and hydrogenating the platinum oxide at room temperature (about 22° C.) while stirring, until hydrogen up-take ceases. The black, elemental platinum, formed thereby, falls to the bottom of the hydrogenation vessel after cessation of the stirring operation. The supernatant liquid is completely clear. Any conventional inert organic solvent can be utilized as the liquid medium for this hydrogenation. Among the preferred liquid media for the hydrogenation are the inert, organic, polar solvents in which the alpha, beta-unsaturated aldehyde can be suitably dissolved. Particularly preferred are the lower alkanols, such as methanol, ethanol, isopropanol and butanol. Also among the preferred liquid media are mixtures of polar and non-polar solvents, such as mixtures of lower alkanols with aliphatic hydrocarbons, such as the saturated aliphatic hydrocarbons of 5–10 carbon atoms, e.g., pentane, hexane, heptane and octane; with cyclic hydrocarbons, such as the saturated cycloaliphatic hydrocarbons of 5 to 7 carbon atoms, e.g. cyclohexane, and the aromatic hydrocarbons of 6 to 14. carbon atoms, e.g., benzene, toluene and xylene; with ethers, such as the dilower alkyl ethers, e.g., diethyl ether, diisopropyl ether, and ethyl butyl ether, and the cyclic ethers, e.g., dioxane; and with esters, such as the lower alkyl alkanoates, e.g., acetic acid methyl, ethyl and butyl esters.

The cobalt is then added to the elemental platinum by mixing the necessary amount of a chosen cobalt salt, such as a cobalt lower alkanoate or halide, e.g., cobalt acetate and cobalt chloride, or cobalt sulphate, preferably dissolved in one of the above named liquid media, while stirring the mixture containing the freshly prepared elemental platinum. The resulting mixture is again hydrogenated at room temperature until the hydrogen uptake comes to a standstill. Preferably, this hydrogenation is carried out in the presence of a small amount of water in the reaction mixture. A particularly preferred amount of water constitutes about 0.5 to 2% by volume based on the total volume of the reaction mixture. The use of the small amount of water increases the solubility of the cobalt salt, thereby facilitating the incorporation of the cobalt with the platinum. The resulting catalyst suspension can be directly utilized for hydrogenating an aldehyde.

In accordance with the process of this application, the elemental cobalt is preferably deposited on the surface of the platinum at the same time the alpha, beta-unsaturated aldehyde is selectively reduced to an alpha, beta-unsaturated alcohol. By this preferred procedure, the platinum-cobalt catalyst is formed in situ during the hydrogenation of the aldehyde.

The ratio of platinum to cobalt, employed in the catalyst of this application, between 100:1 and 1:1 (molar parts), is not critical, and the ratio can be varied depending upon the aldehyde to be reduced. For example, simple aldehydes which, besides the alpha, beta-unsaturated double bond, contain no further unsaturated bonds or hydrogenable groups, can be suitably hydrogenated to the corresponding alpha, beta-unsaturated alcohols with a platinum-cobalt catalyst in which the cobalt portion is relatively small. However for the hydrogenation of aldehydes which, besides the alpha, beta-unsaturated double bond, contain other unsaturated bonds, which may be conjugated, a platinum-cobalt catalyst with an increased cobalt content is desirable.

The optimal composition of the catalyst for a specific substrate can be conveniently determined by experimentation. It has, however, been found generally preferable for the hydrogenation of simple, alpha, beta-unsaturated aldehydes, without additional unsaturated bonds or with only isolated, additional unsaturated bonds, to use a catalyst consisting of about 10 atoms of platinum per atom of cobalt. On the other hand, for hydrogenating highly sensitive, conjugated, unsaturated polyene aldehydes, it is preferred to employ a catalyst consisting of about 2 atoms of platinum per atom of cobalt. Hence, it is generally preferred in carrying out the process of this application to utilize a catalyst containing about 2 to 10 moles of platinum per mole of cobalt.

The platinum-cobalt catalyst used can consist of the pure metals. It can, however, also be supported on an inert carrier. In the process of this application, any conventional, inert carrier can be utilized, such as calcium carbonate and activated carbon. The amount of the carrier material can amount to about 10 to about 80% of the metal content. The platinum-cobalt catalyst supported on a carrier material, such as activated carbon, can be prepared in a conventional manner. For example, such a supported catalyst can be conveniently obtained by placing chloroplatinic acid on activated carbon according to a known process and, then, as described above, hydrogenating the platinum-carbon mixture, resulting after the addition of the cobalt salt solution, up to the completion of the hydrogen uptake.

The platinum-cobalt catalyst of this application can be employed for the reduction of alpha, beta-unsaturated aldehydes as a suspension as well as in isolated form. When, in the preparation of the catalyst, a cobalt salt such as cobalt acetate is used and when one of the simple, non-sensitive aldehydes described above is the substrate to be reduced, then, in most cases, the substrate dissolved in one of the previously named solvents or solvent mixtures can be suitably added to the platinum-cobalt catalyst suspension, as it is formed, and hydrogenated. On the other hand, if one of the above-described, sensitive, alpha, beta-unsaturated aldehydes is to be reduced, then it is preferable to eliminate the anions introduced with the cobalt salt, especially the chloride or sulphate ions before hydrogenation. In such a case, the platinum-cobalt catalyst formed is preferably filtered off under inert gas protection, carefully washed first with water and then with methanol and dried under inert gas protection.

The dry, platinum-cobalt catalyst of this application, when isolated, is a black powder, which is extremely pyrophorus and which ceases to glow under explosion with the slightest free access of air. In the case of storage, the isolated catalyst must therefore be maintained under strict precautions under inert gas.

By way of illustration, the dry, platinum-cobalt catalyst of this application can be isolated by the following procedure. 725 mg. of platinum dioxide is suspended in 250 ml. of methanol and hydrogenated at room temperature (22° C.) and normal pressure (0 p.s.i.g.) until hydrogen is no longer taken up. The suspension is thereafter treated with 90 mg. of cobalt acetate tetrahydrate, 60 ml. of methanol and 6 ml. of water and again hydrogenated up to the standstill of the hydrogen uptake. The platinum-cobalt catalyst obtained is subsequently separated from the reaction solution under nitrogen gasification, washed ion-free with 50 ml. of water, pre-dried with 50 ml. of methanol and thereafter dried with the aid of an IR lamp under continued nitrogen gasification. The dry catalyst can be stored under nitrogen and can be used portion-wise as required under exclusion of air.

In carrying out the preparation of the platinum-cobalt catalysts by hydrogenation and the reduction of the alpha, beta-unsaturated aldehydes in accordance with this application, conditions of temperature and pressure are not critical, and these process steps can be suitably carried out at room temperature and atmospheric pressure. However, greater or lesser temperatures of about 15° to 60° C. and pressures of about 0 to 1000 p.s.i.g. can also be suitably utilized. Preferably, temperatures of 20° to 30° C. and pressures of 0 to 150 p.s.i.g. are utilized in these process steps.

By the process of this application, alpha, beta-unsaturated alcohols can be obtained in almost quantitative yields, of up to 99+%.

The alpha, beta-unsaturated alcohols can be isolated in pure form by conventional work-up procedures. Preferably, the alcohols are isolated by filtering off the catalyst, removing the solvent from the filtrate, and washing and drying the residue.

The examples which follow further illustrate the process of this application.

EXAMPLE 1

250 mg. of platinum dioxide is suspended in 50 ml. of methanol and reduced under normal pressure (0 p.s.i.g. of hydrogen gas) at room temperature (22° C.) up to the termination of the hydrogen uptake.

The platinum suspension is treated with stirring with 1400 mg. of veratric aldehyde dissolved in 50 ml. of methanol and, after addition of 25 mg. of cobalt acetate tetrahydrate and 2 ml. of water, hydrogenated under normal pressure at room temperature up to the standstill of the hydrogen uptake.

The colorless reaction solution is subsequently separated by filtration from the catalyst. The catalyst is back-washed with 20 ml. of methanol. The combined filtrates are evaporated under reduced pressure. The residue is taken up in 200 ml. of methylene chloride. The methylene chloride solution is washed neutral twice with 50 ml. of deionized water each time, dried over calcium chloride and evaporated. There is obtained pure veratryl alcohol with a yield of 96%.

EXAMPLE 2

250 mg. of platinum dioxide is suspended in 50 ml. of methanol and reduced under normal pressure at room temperature up to the termination of the hydrogen uptake. The methanol is thereafter distilled off and replaced by 50 ml. of acetic acid ethyl ester.

The platinum suspension is treated with stirring with 2483.2 mg. of 3-methoxy-19-nor-pregna-1,3,5,17(20)-tetraen-21-al dissolved in 50 ml. of acetic acid ethyl ester and, after addition of 35 mg. of cobalt acetate tetrahydrate and 2 ml. of water, hydrogenated under normal pressure at room temperature up to the standstill of the hydrogen uptake.

The reaction solution is subsequently separated by filtration from the catalyst. The catalyst is back-washed with 30 ml. of acetic acid ethyl ester. The combined filtrates are evaporated under reduced pressure. The residue is taken up in 300 ml. of acetic acid ethyl ester, washed neutral with water, dried over calcium chloride and evaporated. There is obtained 21-hydroxy-3-methoxy-19-nor-pregna-1,3,5,17(20)-tetraene with a yield of 73.0%.

EXAMPLE 3

250 mg. of platinum dioxide is suspended in 50 ml. of methanol and reduced under normal pressure at room temperature up to the termination of the hydrogen uptake.

The platinum suspension is treated with stirring with 2115 mg. of cinnamic aldehyde dissolved in 50 ml. of methanol and, after addition of 100 mg. of cobalt acetate tetrahydrate and 2 ml. of water, hydrogenated under normal pressure at room temperature up to the standstill of the hydrogen uptake.

The colorless reaction solution is subsequently worked-up by separating the solution by filtration from the catalyst. The catalyst is then back-washed with 20 ml. of methanol. The combined filtrates are evaporated under reduced pressure. The residue is taken up in 200 ml. of diethyl ether, washed neutral with water, dried over calcium chloride and evaporated. There is obtained pure cinnamic alcohol with a yield of 99.5%.

EXAMPLE 4

250 mg. of platinum dioxide is suspended in 50 ml. of methanol and reduced under normal pressure at room temperature.

The platinum suspension is treated with stirring with 1618 mg. of alpha-pentyl-cinnamic aldehyde dissolved in 50 ml. of methanol and, after addition of 25 mg. of cobalt acetate tetrahydrate and 2 ml. of water, hydrogenated under normal pressure at room temperature up to the standstill of the hydrogen uptake.

The reaction solution is worked up utilizing the procedure described in the last paragraph of Example 3. There is obtained alpha-pentyl-cinnamic alcohol with a yield of 87%.

EXAMPLE 5

500 mg. of platinum dioxide is suspended in 100 ml. of methanol and reduced under normal pressure at room temperature up to the termination of the hydrogen uptake.

The platinum suspension is treated with stirring with 5200 mg. of alpha-hexyl-cinnamic aldehyde dissolved in 100 ml. of methanol and, after addition of 50 mg. of cobalt acetate tetrahydrate and 4 ml. of water, hydrogenated under normal pressure at room temperature up to the standstill of the hydrogen uptake.

The reaction solution is worked up utilizing the procedure described in the last paragraph of Example 3. There is obtained alpha-hexyl-cinnamic alcohol with a yield of 91.0%.

EXAMPLE 6

250 mg. of platinum dioxide is suspended in 50 ml. of methanol and reduced under normal pressure at room temperature up to the termination of the hydrogen uptake.

The platinum suspension is treated with stirring with 30 mg. of cobalt acetate tetrahydrate, 50 ml. of methanol and 2 ml. of water and, after addition of 1341 mg. of 4-[2,6,6-trimethyl-cyclohex-1-en-1-yl]-2-methyl-but-2-en-1-al, hydrogenated under normal pressure at room temperature up to the standstill of the hydrogen uptake.

The colorless reaction solution is subsequently worked-up by separating the solution by filtration from the catalyst. The catalyst is back-washed with 20 ml. of methanol. The combined filtrates are evaporated under reduced pressure. The residue is taken up in methylene chloride. The solution is washed neutral with water, dried over calcium chloride and evaporated. There is obtained 4-[2,6,6-trimethyl-cyclohex-1-en-1-yl]-2-methyl-but-2-en-1-ol with a yield of 92.4%.

EXAMPLE 7

1000 mg. of platinum dioxide is suspended in 200 ml. of n-butanol and reduced under normal pressure at room temperature up to the termination of the hydrogen uptake.

The platinum suspension is treated with stirring with 60 mg. of cobalt acetate tetrahydrate, 200 ml. of n-butanol and 2 ml. of water and, after addition of 7.31 g of 6-[2,6,6-trimethyl-cyclo-hex-1-en-1-yl]-4-methyl-hexa-2,4-dien-1-al, hydrogenated under normal pressure at room temperature up to the standstill of the hydrogen uptake.

The reaction solution is worked up utilizing the procedure described in the last paragraph of Example 6. There is obtained 6-[2,6,6-trimethyl-cyclohex-1-en-1-yl]-4-methyl-hexa-2,4-dien-1-ol with a yield of 90.5%.

EXAMPLE 8

250 mg. of platinum dioxide is suspended in 30 ml. of isopropanol and reduced under normal pressure at room temperature up to the termination of the hydrogen uptake.

The platinum suspension is treated with stirring with 30 mg. of cobalt acetate tetrahydrate, 70 ml. of methanol and 2 ml. of water and, after addition of 2173.6 mg. of 8-[2,6,6-trimethyl-cyclohex-1-en-1-yl]-2,6-dimethyl-octa-2,4,6-trien-1-al, hydrogenated under normal pressure at room temperature up to the standstill of the hydrogen uptake.

The reaction solution is worked up utilizing the procedure described in the last paragraph of Example 6. There is obtained 8-[2,6,6-trimethyl-cyclohex-1-en-1-yl]-2,6-dimethyl-octa-2,4,6-trien-1-ol with a yield of 93.5%.

EXAMPLE 9

250 mg. of platinum dioxide is suspended in 50 ml. of methanol and reduced under normal pressure at room temperature up to the termination of the hydrogen uptake.

The platinum suspension is treated with stirring with 150 mg. of cobalt acetate tetrahydrate, 50 ml. of methanol and 2 ml. of water and, after addition of 1957 mg. of 9-[2,6,6-trimethyl-cyclohex-1en-1-yl]-3,7-dimethyl-nona-2,4,6,8-tetraen-1-al, hydrogenated under normal pressure at room temperature. The hydrogenation comes to a standstill after the uptake of 6.75 mmol. of hydrogen.

The reaction solution is worked up utilizing the procedure described in the last paragraph of Example 6, in the absence of air. There is obtained 9-[2,6,6-trimethyl-cyclohex-1-en-1-yl]-3,7-dimethyl-nona-2,4,6,8-tetraen-1-ol [13-cis/trans-vitamin A alcohol in a ratio of 1:7] with a yield of 92%.

EXAMPLE 10

250 mg. of platinum dioxide is suspended in 50 ml. of methanol and reduced under normal pressure at room temperature up to the termination of the hydrogen uptake.

The platinum suspension is treated with stirring with 50 mg. of cobalt acetate tetrahydrate, 30 ml. of hexane and 1 ml. of water and, after addition of 2632 mg. of 13-[2,6,6-trimethyl-cyclohex-1-en-1-yl]-2,7,11-trimethyl-trideca-2,6,8,10,12-pentaen4-yn-1-al in 30 ml. of hexane, hydrogenated under normal pressure at room temperature. The hydrogenation comes to a standstill after the uptake of 7.3 mmol. of hydrogen.

The reaction solution is subsequently worked-up by separating the solution by filtration from the catalyst. The catalyst is washed with 20 ml. of methanol. The combined filtrates are evaporated under reduced pressure. The residue is taken up in hexane. The solution is washed neutral with water, dried over calcium chloride and evaporated. There is obtained 13-[2,6,6-trimethyl-cyclohex-1-en-1-yl]-2,7,11-trimethyl-trideca-2,6,8,10,12-pentaen-4-yn-1-ol with a yield of 94.5%.

EXAMPLE 11

250 mg. of platinum dioxide is suspended in 30 ml. of methanol and reduced under normal pressure at room temperature up to the termination of the hydrogen uptake.

The platinum suspension is treated with stirring with 35 mg. of cobalt acetate tetrahydrate, 20 ml. of methanol and 1 ml. of water and, after addition of 3011 mg. of 15-[2,6,6-trimethyl-cyclohex-1-en-1-yl]-4,9,13-trimethyl-pentadeca-2,4,8,10,12,14-hexaen-6-yn-1-al in 50 ml. of hexane, hydrogenated under normal pressure at room temperature. The hydrogenation comes to a standstill after the uptake of 7.85 mmol. of hydrogen.

The reaction solution is worked up utilizing the procedure described in the last paragraph of Example 10. There is obtained 15-[2,6,6-trimethyl-cyclohex-1-en-1-yl]-4,9,13-trimethyl-pentadeca-2,4,8,10,12,14-hexaen-6-yn-1-ol with a yield of 96.0%.

EXAMPLE 12

250 mg. of platinum dioxide is suspended in 30 ml. of methanol and reduced under normal pressure at room temperature up to the termination of the hydrogen uptake.

The platinum suspension is treated with stirring with 30 mg. of cobalt acetate tetrahydrate, 20 ml. of methanol and 2 ml. of water and, after addition of 3340 mg. of 17-[2,6,6-trimethyl-cyclohex-1-en-1-yl]-2,6,11,15-tetramethyl-heptadeca-2,4,6,10,12,14,16-heptaen-8-yn-1-al dissolved in 50 ml. of benzene, hydrogenated under normal pressure at room temperature up to the standstill of the hydrogen uptake.

The colorless reaction solution is subsequently separated by filtration from the catalyst. The catalyst is back-washed with 100 ml. of benzene. The combined filtrates are evaporated under reduced pressure. The residue is taken up in 500 ml. of benzene. The solution is washed neutral with water, dried over calcium chloride and evaporated. There is obtained 17-[2,6,6-trimethyl-cyclohex-1-en-1-yl]-2,6,11,15-tetramethyl-heptadeca-2,4,6,10,12,14,16-heptaen-8-yn-1-ol with a yield of 78%.

EXAMPLE 13

250 mg. of platinum dioxide is suspended in 50 ml. of n-butanol and reduced under normal pressure at room temperature up to the termination of the hydrogen uptake.

The platinum suspension is treated with stirring with 840 mg. of 3-methyl-but-2-en-1-al (prenal) dissolved in 50 ml. of n-butanol and, after addition of 15 mg. of cobalt acetate tetrahydrate and 2 ml. of water, hydrogenated under normal pressure at room temperature up to the standstill of the hydrogen uptake.

The reaction solution is subsequently separated by filtration from the catalyst. The catalyst is back-washed with 20 ml. of n-butanol. The combined filtrates are evaporated under reduced pressure. The residue is taken up in 200 ml. of methylene chloride, washed neutral with water, dried and evaporated. There is obtained 3-methyl-but-2-en-1-ol (prenol) with a yield of 91.4%.

EXAMPLE 14

250 mg. of platinum dioxide is suspended in 50 ml. of methanol and reduced under normal pressure at room temperature up to the termination of the hydrogen uptake.

The platinum suspension is treated with stirring with 1173.6 mg. of 4,4-dimethoxy-3-methyl-but-2-en-1-al dissolved in 50 ml. of methanol and, after addition of 35 mg. of cobalt acetate tetrahydrate and 2 ml. of water, hydrogenated under normal pressure at room temperature up to the standstill of the hydrogen uptake.

The reaction solution is subsequently separated by filtration from the catalyst. The catalyst is back-washed with 20 ml. of methanol. The combined filtrates are evaporated under reduced pressure. There is obtained 4,4-dimethoxy-3-methyl-but-2-en-1-ol with a yield of 80.0%.

EXAMPLE 15

250 mg. of platinum dioxide is suspended in 50 ml. of methanol and reduced under normal pressure at room temperature up to the termination of the hydrogen uptake.

The platinum suspension is treated with stirring with 1345 mg. of 6-acetoxy-3-methyl-hexa-2,4-dien-1-al dissolved in 50 ml. of methanol and, after addition of 35 mg. of cobalt acetate tetrahydrate and 2 ml. of water, hydrogenated under normal pressure at room temperature up to the standstill of the hydrogen uptake.

The reaction solution is worked up utilizing the procedure described in the last paragraph of Example 3. There is obtained 6-acetoxy-3-methyl-hexa-2,4-dien-1-ol with a yield of 90.7%.

EXAMPLE 16

30 g. of platinum dioxide and 30 g. of Norit XXX activated carbon are suspended in 2000 ml. of methanol and reduced under normal pressure at room temperature up the termination of the hydrogen uptake.

The platinum suspension is treated with stirring with 5700 g. of trans-3,7-dimethyl-2,6-octadien-1-al (citral) dissolved in 8000 ml. of methanol and, after addition of 3.15 g. of cobalt acetate tetrahydrate and 45 ml. of water, hydrogenated under normal pressure at room temperature up to the standstill of the hydrogen uptake. The duration of hydrogenation is 6.5 hours, and the hydrogen consumption is 948 l.

The colorless reaction solution is separated by filtration from the catalyst. The catalyst is back-washed with 200 ml. of methanol. The combined filtrates are evaporated under reduced pressure. There is obtained a residue, containing 95% 3,7-dimethyl-2,6-octadien-1-ol (geraniol).

EXAMPLE 17

250 mg. of platinum dioxide is suspended in 50 ml. of n-butanol and reduced under normal pressure at room temperature up to the termination of the hydrogen uptake.

The platinum suspension is treated with stirring with 1860 mg. of 3,7,11-trimethyl-2,6,10-dodecatrien-1-al (farnesal) dissolved in 50 ml. of n-butanol and, after addition of 35 mg. of cobalt acetate tetrahydrate and 2 ml. of water, hydrogenated under normal pressure at room temperature up to the standstill of the hydrogen uptake.

The reaction solution is worked up utilizing the procedure described in the last paragraph of Example 3. There is obtained 3,7,11-trimethyl-2,6,10-dodecatrien-1-ol (farnesol) with a yield of 91.0%.

EXAMPLE 18

250 mg. of platinum dioxide is suspended in 50 ml. of methanol and reduced under normal pressure at room temperature up to the termination of the hydrogen uptake.

The platinum suspension is treated with stirring with 3658 mg. of alpha-naphthyl aldehyde dissolved in 50 ml. of methanol and, after addition of 30 mg. of cobalt acetate tetrahydrate, hydrogenated under normal pressure at room temperature up to the end of hydrogen uptake.

The colorless reaction solution is subsequently worked-up by separating the solution by filtration from the catalyst. The catalyst is back-washed with 20 ml. of methanol. The combined filtrates are evaporated. The crystalline precipitate is recrystallized once from methanol. There is obtained pure alphanaphthyl carbinol with a yield of 95.5%.

EXAMPLE 19

250 mg. of platinum dioxide is suspended in 50 ml. of methanol and reduced under normal pressure at room temperature up to the termination of the hydrogen uptake.

The platinum suspension is treated with stirring with 3120 mg. of beta-naphthyl aldehyde dissolved in 50 ml. of methanol and, after addition of 30 mg. of cobalt acetate tetrahydrate, hydrogenated under normal pressure at room temperature up to the standstill of the hydrogen uptake.

The reaction solution is worked up utilizing the procedure described in the last paragraph of Example 18. There is obtained pure beta-naphthyl carbinol with a yield of 54.5%.

EXAMPLE 20

500 mg. of platinum dioxide is suspended in 50 ml. of methanol and reduced under normal pressure at room temperature up to the termination of the hydrogen uptake.

The platinum suspension is treated with stirring with 4800 mg. of furfural dissolved in 50 ml. of methanol and, after addition of 50 mg. of cobalt tetrahydrate, hydrogenated under normal pressure at room temperature up to the standstill of the hydrogen uptake.

The reaction solution is separated by filtration from the catalyst. The filtrate is dried and distilled. There is obtained pure furfuryl alcohol with a yield of 96.5%.

EXAMPLE 21

5 g. of platinum dioxide is suspended in 100 ml. of methanol and reduced under normal pressure at room temperature up to the termination of the hydrogen uptake.

The platinum suspension is treated with stirring with 178.3 g. of 2,6,6-trimethyl-1-cyclohexen-1-carboxaldehyde (beta-cyclocitral) dissolved in 1400 ml. of methanol and, after addition to 1 g. of cobalt acetate tetrahydrate and 10 ml. of methanol, hydrogenated under normal pressure at room temperature up to the standstill of the hydrogen uptake.

The reaction solution is subsequently separated by filtration from the catalyst. The filtrate is concentrated The residue is taken up in 500 ml. of diethyl ether, and the ether solution is washed once with 100 ml. of deionized water, dried and evaporated. There is obtained pure 2,6,6-trimethyl-1-cyclo-hexen-1-methanol (beta-cyclogeraniol) with a yield of 91.5%.

EXAMPLE 22

5 g. of platinum dioxide and 5 g. of Norit activated carbon are suspended in 500 ml. of methanol and reduced under normal pressure at room temperature up to the termination of the hydrogen uptake.

The platinum suspension is treated with stirring with 71.0 g. of 6-acetoxy-4-methyl-hexa-2,4-dien-1-al dissolved in 1500 ml. of methanol and, after addition of 600 mg. of cobalt acetate tetrahydrate and 10 ml. of water, hydrogenated under normal pressure at room temperature up to the standstill of the hydrogen uptake.

The reaction solution is subsequently separated by filtration from the catalyst. The filtrate is evaporated. The residue is taken up in diethyl ether. The ether solution is washed once with water, dried and evaporated. There is obtained pure 6-acetoxy-4-methyl-hexa-2,4-dien-1-ol with a yield of 94.8%.

EXAMPLE 23

250 mg. of platinum dioxide is suspended in 50 ml. of methanol and reduced under normal pressure at room temperature up to the termination of the hydrogen uptake.

The platinum suspension is treated with stirring with 900 mg. of 8-acetoxy-2,6-dimethyl-octa-2,4,6-trien-1-al dissolved in 50 ml. of methanol and, after addition of 35 mg. of cobalt acetate tetrahydrate and 1.0 ml. of water, hydrogenated under normal pressure at room temperature up to the standstill of the hydrogen uptake.

The reaction solution is subsequently separated by filtration from the catalyst. The filtrate is evaporated. The residue is taken up in diethyl ether. The ether extract is washed with water, dried and evaporated. There is obtained pure 8-acetoxy-2,6-dimethyl-octa-2,4,6-trien-1-ol with a yield of 89.7%.

EXAMPLE 24

250 mg. of platinum dioxide is suspended in 50 ml. of methanol and reduced under normal pressure at room temperature up to the termination of the hydrogen uptake.

The platinum suspension is treated with stirring with 1800 mg. of 7-ethyl-3-methyl-nona-2,6-dien-1-al dissolved in 50 ml. of methanol and, after addition of 60 mg. of cobalt acetate tetrahydrate and 0.5 ml. of water, hydrogenated under normal pressure at room temperature up to the standstill of the hydrogen uptake.

The reaction solution is subsequently separated by filtration from the catalyst. The filtrate is concentrated and distilled. There is obtained pure 7-ethyl-3-methyl-nona-2,6-dien-1-ol with a yield of 93.4%.

I claim:

1. A process for preparing an alpha, beta-unsaturated alcohol of the formula:

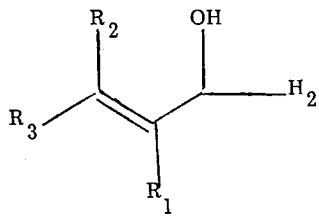

wherein $R_1$ and $R_2$ are hydrogen or lower alkyl; and $R_3$ is hydrocarbyl, cyclohydrocarbyl or aryl; or $R_1$ and $R_3$ taken together or $R_2$ and $R_3$ taken together form a cyclohydrocarbyl or aryl group; said hydrocarbyl being unsubstituted or substituted with a lower alkyl, lower alkoxy, lower alkanoyloxy or cyclohydrocarbyl substituents and said aryl and cyclohydrocarbyl being unsubstituted or substituted in one or more positions with lower alkyl, lower alkoxy or lower alkanoyloxy substituents; comprising hydrogenating with hydrogen gas an alpha, beta-unsaturated aldehyde of the formula:

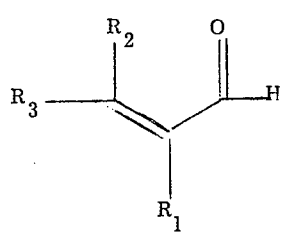

wherein $R_1$, $R_2$ and $R_3$ are as above; said hydrogenation being carried out in an inert organic polar solvent medium in the presence of a catalyst suspended in said medium, said catalyst being elemental platinum with its surface coated with elemental cobalt where the catalyst contains from 1 to 100 moles of elemental platinum per mole of cobalt, said hydrogenation being carried out at pressures of from about 0 to 1,000 psig and temperatures of from about 15° C. to 60° C.

2. The process of claim 1 wherein said polar solvent is a lower alkanol.

3. The process of claim 1 wherein said aldehyde is hydrogenated in a mixture of a polar and a non-polar solvent.

4. The process of claim 3 wherein said non-polar solvent is an aliphatic hydrocarbon, a cycloaliphatic hydrocarbon, an aromatic hydrocarbon, a dilower alkyl ether, a cyclic ether or a lower alkyl lower alkanoate.

5. The process of claim 4 wherein said polar solvent is methanol, ethanol, isopropanol or butanol.

6. The process of claim 1 wherein said catalyst comprises about 2 to 10 moles of platinum per mole of cobalt.

7. The process of claim 1 wherein $R_2$ and $R_3$, taken together, form a cyclohydrocarbyl group and $R_1$ is hydrogen.

8. The process of claim 7 wherein said aldehyde is cyclopentylidene acetaldehyde, cyclohexylidene acetaldehyde or 2,6,6-trimethyl-cyclohexylidene acetaldehyde or 3-methoxy-19-nor-pregna-1,3,5,17(20)-tetraen-21-al.

9. The process of claim 1 wherein $R_1$ and $R_2$ are hydrogen or lower alkyl and $R_3$ is cyclohydrocarbyl or aryl.

10. The process of claim 9 wherein said aldehyde is cinnamaldehyde or 3-(3-methyl-cyclohex-3-en-1-yl)-but-2-en-1-al.

11. The process of claim 1 wherein said aldehyde is of the formula:

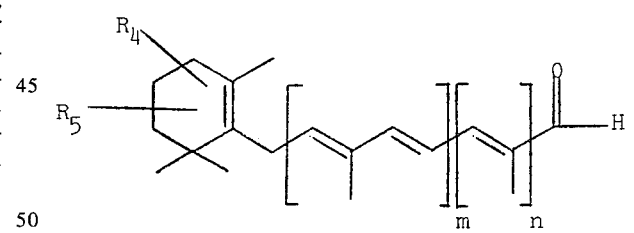

$m$ and $n$ are the integer 0 or 1; $m$ or $n$ being 1; $R_4$ is hydrogen; and $R_5$ is hydrogen.

12. The process of claim 11 wherein said aldehyde is 4-[2,6,6-trimethyl-cyclohex-1-en-1-yl]-2-methyl-but-2-en-1-al.

13. The process of claim 1 wherein said aldehyde is of the formula:

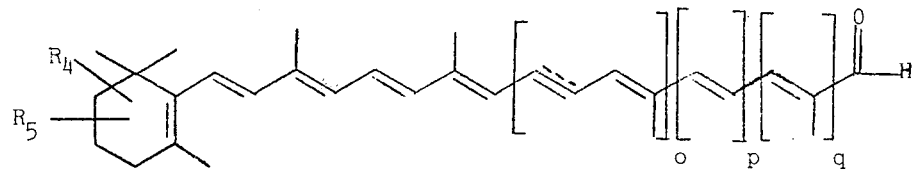

$R_4$ and $R_5$ are as above; the dotted bond can optionally be hydrogenated; and $o$, $p$ and $q$ are the integer 0 or 1; provided that when $o$ is 0, $p$ and $q$ or 0, when $p$ is 1, $o$ is 1 and when $p$ is 0, $q$ is 0.

14. The process of claim 13 wherein said aldehyde is 9-[2,6,6-trimethyl-cyclohex-1-en-1-yl]-3,7-dimethyl-nona-2,4,6,8-tetraen-1-al.

15. The process of claim 1, wherein said hydrogenation is carried out in the presence of about 0.5 to 2.0% by volume of water in the reaction mixture.

* * * * *